United States Patent [19]

Kakimoto et al.

[11] Patent Number: 4,778,567
[45] Date of Patent: Oct. 18, 1988

[54] METHOD FOR PURIFICATION OF ETHYLENE OXIDE AND RECOVERY OF HEAT THEREOF

[75] Inventors: Yukihiko Kakimoto; Masayuki Sawada; Yoshiaki Kajimoto, all of Yokohama; Isamu Kiguchi, Zushi, all of Japan

[73] Assignee: Nippon Shokubai Kagaku Kogyo Co., Osaka, Japan

[21] Appl. No.: 880,734

[22] Filed: Jul. 1, 1986

[30] Foreign Application Priority Data

| Jul. 3, 1985 [JP] | Japan | 60-144642 |
| Jul. 10, 1985 [JP] | Japan | 60-150003 |
| Mar. 28, 1986 [JP] | Japan | 61-68793 |
| Apr. 2, 1986 [JP] | Japan | 61-74357 |

[51] Int. Cl.$^4$ ............................................. B01D 3/00
[52] U.S. Cl. ........................................ 203/23; 203/25; 203/27; 203/75; 203/77; 203/78; 203/80; 203/DIG. 4; 203/DIG. 8; 203/DIG. 9; 203/DIG. 25; 549/541
[58] Field of Search ............... 203/DIG. 4, DIG. 25, 203/14, 21, 25, 27, 23, DIG. 8, 75, 77, 78, 80, DIG. 9; 549/541

[56] References Cited

U.S. PATENT DOCUMENTS

| 2,325,576 | 7/1943 | Balcar | 549/541 |
| 2,615,901 | 10/1952 | McClellan | 549/541 |
| 2,771,473 | 11/1956 | Courter | 549/541 |
| 2,775,600 | 12/1956 | Maslan | 549/541 |
| 3,165,539 | 1/1965 | Lutz | 549/541 |
| 3,217,466 | 11/1965 | Bogart | 55/48 |
| 3,388,046 | 6/1968 | Hendrix | 203/27 |
| 3,745,092 | 7/1973 | Vanderwater | 203/42 |
| 3,964,980 | 6/1976 | Ozero | 203/69 |
| 4,028,070 | 6/1977 | Uchii et al. | 55/48 |
| 4,033,617 | 7/1977 | Cocuzza et al. | 203/36 |
| 4,134,797 | 1/1979 | Ozero | 203/75 |
| 4,304,639 | 12/1981 | Hardy et al. | 203/36 |
| 4,447,318 | 5/1984 | Ogura et al. | 203/25 |

FOREIGN PATENT DOCUMENTS 0115535 6/1985 Japan ........................... 203/25

Primary Examiner—David L. Lacey
Assistant Examiner—V. Manoharan
Attorney, Agent, or Firm—Omri M. Behr

[57] ABSTRACT

In the purification of ethylene oxide from an ethylene oxide-containing reaction formation gas produced by catalytic gas-phase oxidation of ethylene with a molecular oxygen containing gas, external thermal energy required for heating an ethylene oxide refiner is economized by a method which utilizes the diffusate obtained from the top of an ethylene oxide stripper as a heat source for the refiner. Further, the bottom liquid of the stripper can be used as a heat source for ethylene oxide refiner and/or a light ends stripper.

11 Claims, 7 Drawing Sheets

METHOD FOR PURIFICATION OF ETHYLENE OXIDE AND RECOVERY OF HEAT THEREOF

BACKGROUND OF THE INVENTION

1. Field of the Invention

This invention relates to a method for the purification of ethylene oxide. More particularly this invention relates to a method for the purification of ethylene oxide by the steps of introducing the gas formed by catalytic gas-phase oxidation of ethylene with a molecular oxygen-containing gas and consequently containing ethylene oxide into an ethylene oxide absorber and led into counterflow contact therein with an absorbent liquid, circulating the gas emanating from the top of the ethylene oxide absorber to the step for oxidation of ethylene, supplying the ethylene oxide-containing bottom liquid of the ethylene oxide absorber to an ethylene oxide stripper, allowing the ethylene oxide stripper to obtain ethylene oxide through diffusion via the top thereof, condensing the resulting distillate containing ethylene oxide and water, separating the water from the distillate in a dehydrator, separating a more volatile component from the distillate in a light ends stripper, and subsequently rectifying the remaining ethylene oxide in an ethylene oxide refiner, which method is characterized by economizing the energy for heating the ethylene oxide refiner and the light ends stripper.

2. Description of Prior Art

Ethylene oxide is generally purified as follows. The catalytic gas-phase oxidation of ethylene with a molecular oxygen-containing gas over a silver catalyst produces a reaction product gas containing ethylene oxide. This gas is led to an ethylene oxide absorber and brought into counterflow contact therein with an absorbent liquid having water as a main component thereof so as to effect recovery of an aqueous ethylene oxide solution. Then, this aqueous solution is forwarded to an ethylene oxide stripper and, by heating the bottom of the stripper, is enabled to obtain ethylene oxide through diffusion. The aqueous solution which now contains substantially no ethylene oxide is withdrawn via the bottom of the stripper to be used again as an absorbent liquid. The diffusate departing from the top of the stripper and containing ethylene oxide, water, carbon dioxide, inert gases (nitrogen, argon, methane, ethane, etc.), low-boiling impurities such as formaldehyde, and high-boiling impurities such as acetaldehyde and acetic acid is purified by being passed through the step of dehydration, the step of separation of more volatile components, and the step for separation of heavy-duty components, to give rise to ethylene oxide. Several methods for purification of ethylene oxide have been proposed. (Refer, for example, to U.S. Pat. Nos. 3,165,539; 2,771,473; 4,028,070; 3,097,215; 3,217,466; 3,745,092; 3,729,899; 3,766,714; and 3,964,980.)

The method heretofore known to the art will be described specifically below.

With reference to FIG. 1, ethylene is subjected to catalytic gas-phase oxidation with a molecular oxygen-containing gas in the presence of a silver catalyst to produce a reaction product gas containing ethylene oxide. This gas is passed through a conduit 1 and fed to the lower part of an ethylene oxide absorber 2 in the form of a packed tower or a tray tower. An absorbent liquid is introduced via a conduit 3 into the upper part of the ethylene oxide absorber 2 and brough into counterflow contact in the tower with the reaction product gas to recover not less than 99% by weight of the ethylene oxide present in the reaction product gas. Such gases as the portion of ethylene oxide which has escaped being absorbed, oxygen, carbon dioxide, inert gases (nitrogen, argon, methane, and ethane), aldehydes, and acidic substances departing from the top of the ethylene oxide absorber 2 are forwarded via a conduit 4 and circulated to the step of carbon dioxide absorption and/or the step of oxidation. In this step of absorption, such low-boiling impurities as formaldehyde and such high-boiling impurities as acetaldehyde and acetic acid which are formed in the step of oxidation of ethylene besides ethylene, oxygen, carbon dioxide, and inert gases (nitrogen, argon, methane, and ethane), let alone ethylene oxide, are absorbed all at once in their substantial proportions. The bottom liquid of the ethylene oxide absorber 2 is passed through a conduit 5 to a heat exchanger 6, there to exchange heat with the bottom liquid of an ethylene oxide stripper and gain in temperature to 70° to 110° C. The hot bottom liquid is then passed through a conduit 7 to a gas-liquid separation tank 8. The more volatile portion of inert gas containing ethylene oxide and water partly is separated via a conduit 9. The absorbent liquid left behind after the more volatile gas has been expelled by flushing is passed through a conduit 10 and introduced to the upper part of an ethylene oxide stripper 11 kept under top pressure of 0.1 to 2 kg/cm$^2$G at a top temperature in the range of 85° to 120° C. and heated in a conduit 13 with a heating medium such as steam or a heat medium (produced by The Dow Chemical Company and marketed under trademark designation of "Dowtherm") circulated through a reboiler 12 annexed to the ethylene oxide stripper 11 or heated directly by feeding steam to the bottom of the ethylene oxide stripper 11. As the result, not less than 99% by weight of the ethylene oxide contained in the absorbent liquid is obtained through diffusion. Part of the bottom liquid of the ethylene oxide stripper containing substantially no ethylene oxide and having a temperature of 100° to 150° C. is withdrawn via the bottom of the ethylene oxide stripper 11 and forwarded via a conduit 15 to the heat exchanger 6, there to exchange heat with the bottom liquid of the ethylene oxide absorber 2. The bottom liquid consequently deprived of heat is passed through a conduit 16 and further cooled by a cooler 17 having cooling water circulated through conduits 18 and 19 therein. Then, fresh water is introduced via a conduit 21 for the purpose of adjusting the ethylene glycol concentration in the absorbent liquid. The absorbent liquid is replenished with aqueous potassium hydroxide solution when necessary for the adjustment of the pH of the liquid. For the adjustment of the anti-foam agent concentration in the absorbent liquid, an anti-foam agent may be introduced into the ethylene oxide absorber 2. To prevent the ethylene glycol by produced in the hydrolysis of ethylene oxide and water, such low-boiling impruities as formaldehyde, and such high-boiling impurities as acetaldehyde and acetic acid from increasing in the absorbent liquid between the step for oxidation of ethylene with molecular oxygen and the step for stripping of ethylene oxide, the bottom liquid of the ethylene oxide stripper 11 is withdrawn via conduits 14 and 22 through the bottom of the ethylene oxide stripper 11 and forwarded to the step for concentration of the by-produced ethylene glycol.

In the meantime, the vapor containing ethylene oxide obtained via the top of the ethylene oxide stripper 11 is forwarded via a conduit 23 to a condenser 24 having cooling water circulated through conduits 25 and 26 therein. The condensate consequently produced is returned via a conduit 27 to the top of the ethylene oxide stripper 11 and the vapor which has escaped being condensed is introduced via a conduit 28 to a dehydrator 29.

The vapor is heated by either being passed through a conduit 31 which is kept heated with a heating medium such as steam or Dowtherm by a reboiler 30 connected to the dehydrator 29 or being directly heated owing to the introduction of steam to the lower part of the dehydrator 29. The water containing no ethylene oxide is withdrawn via a conduit 32 from the bottom of the dehydrator 29.

From the top of the dehydrator 29, the vapor containing ethylene oxide is forwarded via a conduit 33 to a condenser 34 having cooling water or brine circulated through conduits 35 and 36 therein. The condensate consequently formed is returned via a conduit 37 to the top of the dehydrator 29. The vapor which has escaped being condensed in the condenser 34 is introduced via a conduit 39 to an ethylene oxide vent-scrubber (not shown). The remaining part of the condensate in the condenser 34 is introduced via a conduit 38 to a light ends stripper 40.

The condensate is heated by being passed through a conduit 42 kept heated with a heating medium such as steam or Dowtherm by a reboiler 41 which is annexed to the light ends stripper 40. From the top of the light ends stripper 40, the vapor containing ethylene oxide is forwarded via a conduit 43 to a condenser 44. The condensate consequently formed is returned via a conduit 47 to the top of the light ends stripper 40. The vapor which has escaped being condensed is introduced via a conduit 48 to an ethylene oxide vent-scrubber (not shown) for the recovery of ethylene oxide.

In the meantime, from the bottom of the light ends stripper 40, the ethylene oxide separated from the more volatile component is introduced via a conduit 49 to an ethylene oxide refiner 50.

The bottom liquid is heated by being passed through a conduit 59 kept heated with a heating medium such as steam or Dowtherm by a reboiler 58 which is annexed to the ethylene oxide refiner 50. A steam of pressure of 0.5 to 3.0 kg/cm$^2$G is introduced via a conduit 59 to the reboiler 58 annexed to the ethylene oxide refiner 50. Then, rectification is carried out with the bottom temperature of the ethylene oxide refiner 50 maintained at 35° to 85° C. and the bottom pressure of the tower maintained 1.2 to 8.2 kg/cm$^2$G. The ethylene oxide vapor of the top temperature of 29° to 81° C. and the top pressure of 1.0 to 8.0 kg/cm$^2$G was withdrawn via the top of the ethylene oxide refiner and forwarded via a conduit 51 to a condenser 52, there to be liquefied. Part of the liquefied ethylene oxide is passed through a conduit 56 and introduced as a reflux liquid to the top of the ethylene oxide refiner 50. The remaining part of the liquefied ethylene oxide is withdrawn via a conduit 57 as an ethylene oxide product.

The vapor which has escaped being condensed in the condenser 52 of the ethylene oxide refiner 50 is introduced via a conduit 55 to the ethylene oxide vent-scrubber (not shown) for recovery of ethylene oxide.

The bottom liquid of the ethylene oxide refiner 50 is withdrawn via a conduit 67 when necessary for the separation of heavy-duty fractions of such high-boiling impurities as acetaldehyde, water, acetic acid etc.

The method for the purification of ethylene oxide described above, however, is not satisfactory in terms of the recovery of the heat of condensation of the vapor obtained through the top of the ethylene oxide stripper and recovery of the thermal energy possessed by the liquid withdrawn through the bottom of the ethylene oxide stripper. Thus, this method has entailed the disadvantage that a large volume of heat is wastefully discharged from the system. The conventional method has imposed the rule of causing the bottom liquid of the ethylene oxide stripper which has a temperature of 100° to 150° C. to exchange heat with the bottom liquid of the ethylene oxide absorber thereby effecting recovery of heat and thereafter cooling the bottom liquid and reclaiming the cooled bottom liquid as an absorbent liquid for use in the ethylene oxide absorber. Further, the method for the purification of ethylene oxide has entailed the disadvantage that the heating carried out in the ethylene oxide refiner consumes a large volume of heating steam.

As the result of our research to saving energy in the above process for purification of ethylene oxide, we have eventually found that the energy possessed by the bottom liquid of the ethylene oxide stripper and possessed by the top vapor thereof can be utilized effectively.

An object of this invention, therefore, is to provide a novel method for the purification of ethylene oxide.

Another object of this invention is to provide a method for the purification of ethylene oxide, which promotes effective utilization of the energy of the top vapor of an ethylene oxide stripper and/or that of the bottom liquid thereof.

SUMMARY OF THE INVENTION

The objects described above are accomplished by a method for the purification of ethylene oxide by the steps of introducing the gas formed by catalytic gas-phase oxidation of ethylene with a molecular oxygen-containing gas and consequently containing ethylene oxide into an ethylene oxide absorber and led into counterflow contact therein with an absorbent liquid, circulating part of the gas emanating from the top of the ethylene oxide absorber to the step for oxidation of ethylene, supplying the ethylene oxide-containing bottom liquid of the ethylene oxide absorber to an ethylene oxide stripper, allowing the ethylene oxide stripper to obtain ethylene oxide through diffusion via the top thereof, condensing the resulting distillate containing ethylene oxide and water, separating the water from the distillate in a dehydrator, separating a more volatile component from the distillate in a light ends stripper, and subsequently rectifying the remaining ethylene oxide in an ethylene oxide refiner, which method is characterized by using the diffusate literated from the ethylene oxide stripper as a heat source for the ethylene oxide refiner.

The aforementioned objects are further accomplished, in the aforementioned purification of ethylene oxide, by a method for the purification of ethylene oxide, which comprises leading part of the liquid withdrawn from the bottom of the ethylene oxide stripper to the ethylene oxide absorber to be used as an absorbent liquid therein, causing the liquid to exchange heat with the bottom liquid from the absorber in a heat exchanger, then recovering thermal energy possessed by the absorbent liquid by the use of a heat pump thereby inducing generation of steam and using the generated steam as a heat source for the purification of ethylene oxide.

The aforementioned objects are also accomplished, in the aforementioned purification of ethylene oxide, by a method for the purification of ethylene oxide, which comprises using part of the liquid withdrawn from the bottom of the ethylene oxide stripper as a heat source for the ethylene oxide refiner or the light ends stripper or both.

PREFERRED EMBODIMENT OF THE INVENTION

Figure 1:
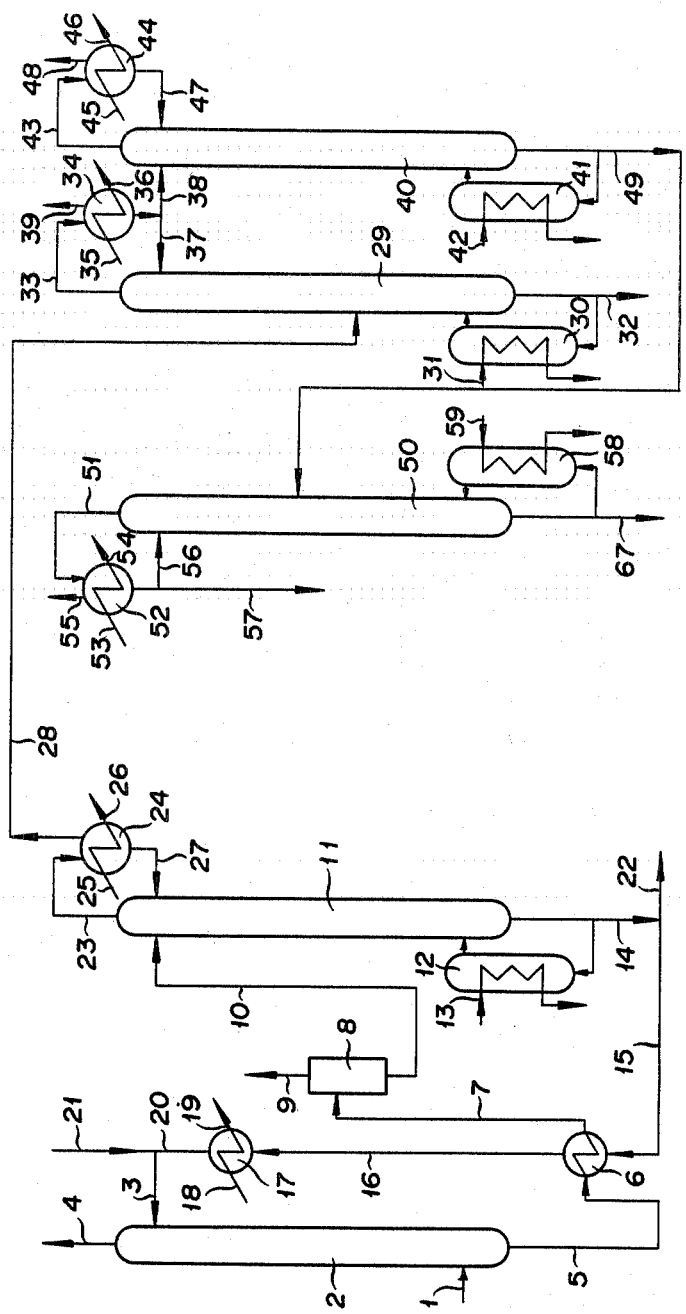
FIG. 1 is a flow chart illustrating a typical known method for the purification of ethylene oxide.

In the present invention, the temperature of the absorbent liquid which is introduced to the ethylene oxide absorber is in the range of 5° to 40° C., preferably 10° to 35° C. The absorbent liquid is controlled so that the pH of the liquid will maintain in the range of 5 to 12, preferably 6 to 11, the ethylene glycol concentration in the range of 1 to 40% by weight, preferably 5 to 30% by weight, the anti-foam agent concentration at or above 0.1 ppm, preferably in the range of 1 to 100 ppm, and the water concentration in the range accounting for the balance. For the ethylene glycol concentration in the absorbent liquid to remain constant, part of the absorbent liquid being circulated through the ethylene oxide absorber and the ethylene oxide stripper is withdrawn through the bottom of the absorbent liquid and forwarded to the by-produced ethylene glycol concentration tower, there to be regulated when necessary by addition of fresh water. The adjustment of the pH is desired to be effected by the addition of a compound such as the hydroxide of an alkali metal like potassium or sodium or a carbonate thereof which are soluble in the absorbent liquid. Specifically, this additive is desired to be potassium hydroxide or sodium hydroxide.

As the anti-foam agent for use in the composition of the absorbent liquid, any of the anti-foam agents can be used which are inactive in the by-produced ethylene glycol, for example, and are capable of defoaming the absorbent liquid. A water-soluble silicone emulsion which is a typical example of such anti-foam agents is used advantageously because it excels in dispersibility, stability of dilution, and thermal stability in the absorbent liquid.

As concerns the operation conditions for the ethylene oxide absorber, the ethylene oxide concentration in the gas formed by the reaction is in the range of 0.5 to 5% by volume, preferably 1.0 to 4% by volume and the working pressure of the ethylene oxide absorber is in the range of 2 to 40 kg/cm$^2$G, preferably 10 to 30 kg/cm$^2$G. As concerns the operation conditions for the ethylene oxide stripper, the top pressure of the ethylene oxide stripper is in the range of 0.1 to 2 kg/cm$^2$G, preferably 0.3 to 0.6 kg/cm$^2$G, the top temperature of the ethylene oxide stripper is in the range of 85° to 120° C., the bottom temperature of the ethylene oxide stripper is in the range of 100° to 150° C., and the ethylene oxide concentration in the bottom of the ethylene oxide stripper is not more than 30 ppm, preferably not more than 0.5 ppm.

In a method comprising the steps of introducing the gas produced by catalytic gas-phase oxidation of ethylene with a molecular oxygen-containing gas and consequently containing ethylene oxide into an ethylene oxide absorber to be brought into counterflow contact therein with an absorbent liquid, circulating part of the gas emanating from the top of the ethylene oxide absorber to the step for oxidation of ethylene oxide, supplying the ethylene oxide-containing bottom liquid of the ethylene oxide absorber to an ethylene oxide stripper, allowing ethylene oxide to be obtained through diffusion from the top of the ethylene oxide stripper, causing the liquid withdrawn from the bottom of the ethylene oxide stripper to exchange heat with the bottom liquid of the ethylene oxide absorber in a heat exchanger, cooling the resulting liquid in a cooler, leading the cooled liquid to the ethylene oxide absorber to be used as an absorbent liquid again therein, and forwarding the remaining liquid to a by-produced ethylene glycol concentration tower for the concentration of the ethylene glycol contained in the liquid, the characteristic of this invention resides in recovering the thermal energy possessed by the vapor obtained through diffusion from the ethylene oxide stripper and effectively utilizing the recovered thermal energy.

For this purpose, the present invention adopts a method which comprises forwarding the vapor from the top of the ethylene oxide stripper to a reboiler of the ethylene oxide refiner, subjecting the diffusate to heat exchange and consequently liquefying the diffusate, returning the condensed liquid to the top of the ethylene oxide stripper, and supplying the uncondensed gas to a dehydrator.

In the present invention, the temperature of the liquid introduced to the dehydrator maintains in the range of 5° to 60° C., preferably 10° to 50° C., and the ethylene oxide concentration in the steam so introduced is in the range of 80 to 98% by weight.

As concerns the operation conditions for the ethylene oxide dehydrator, the top pressure of the dehydrator is in the range of 0.1 to 2 kg/cm$^2$G, preferably 0.3 to 0.6 kg/cm$^2$G, the top temperature of the dehydrator is in the range of 10° to 40° C., and the bottom temperature of the dehydrator is in the range of 100° to 150° C. The ethylene oxide concentration in the bottom of the dehydrator is not more than 100 ppm, preferably not more than 10 ppm.

In the present invention, the temperature of the liquid introduced to the light ends stripper is in the range of 0° to 50° C., preferably 5° to 30° C. The liquid so introduced has ethylene oxide as its major component and contains minute amounts of formaldehyde and other aldehydes besides water.

As concerns the operation conditions for the light ends stripper, the top pressure of the light ends stripper is in the range of 1 to 10 kg/cm$^2$G, preferably 3 to 7 kg/cm$^2$G, the top temperature of the light ends stripper is in the range of 30° to 90° C., and the bottom temperature of the light ends stripper is in the range of 30° to 90° C.

The ethylene oxide concentration in the bottom of the light ends stripper is not less than 99.5 by weight, preferably not less than 99.95% by weight.

In the present invention, the ethylene oxide refiner is either a tray tower or a packed tower. In the case of the tray type distillation tower, examples of the type of tray include bubble cap tray, uniflux tray, Turbogrid tray, lip tray, Flexy tray, sieve tray, and ballast tray. Examples of the packing for the packed type refiner are Raschigrings, Pall rings, saddleshaped rings, spiral rings, MacMahon packing, Intalox metal packing, packing materials possessing pressure drop of not more than 10 mmHg per theoretical step, and superposed metal nets of woven or knit pattern.

The temperature of the liquid which is introduced to the ethylene oxide refiner in the present invention is in the range of 30° to 90° C., preferably 50° to 70° C. The composition of the liquid so introduced is controlled so that the ethylene oxide concentration will be not less than 99.5% by weight, preferably not less than 99.95% by weight.

As concerns the operation conditions for the ethylene oxide refiner, the top pressure of the refiner is in the range of 1.0 to 8.0 kg/cm$^2$G, preferably 1.2 to 5.0 kg/cm$^2$G, the top temperature of the refiner is in the range of 29° to 81° C., the bottom temperature of the refiner is in the range of 35° to 85° C., and the ethylene oxide concentration in the bottom of the refiner is in the range of 30 to 90% by weight, preferably 40 to 80% by weight.

In this invention, the bottom liquid of the ethylene oxide refiner is a heavy-duty component consisting of such high-boiling impurities as acetaldehyde, water, acetic acid etc.

Now, the present invention will be described more specifically below with reference to the drawings.

Figure 2:
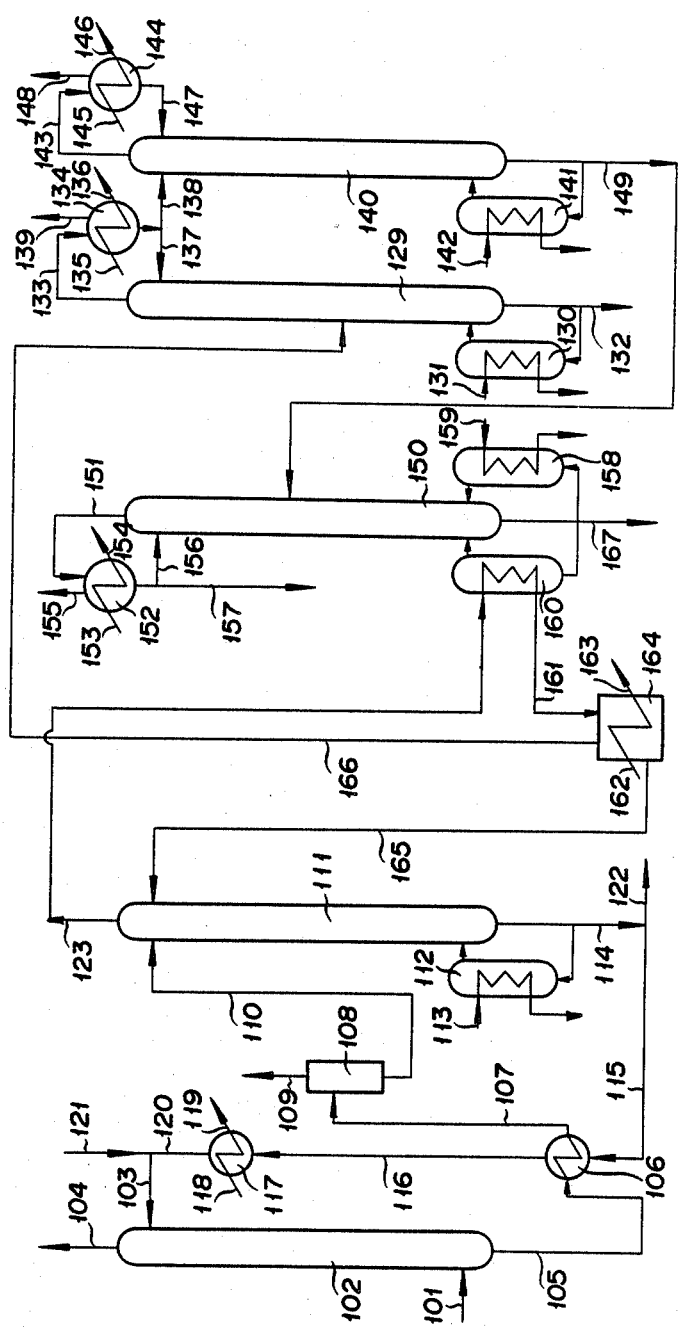
FIG. 2 is a flow chart illustrating a typical method for the purification of ethylene oxide in accordance with the present invention.

As illustrated in FIG. 2, the gas resulting from the catalytic gas-phase oxidation of ethylene with a molecular oxygen-containing gas and consequently containing ethylene oxide is introduced via a conduit 101 to the lower part of a packed type or tray type ethylene oxide absorber 102. An absorbent liquid is introduced via a conduit 103 into the ethylene oxide absorber 102 and brought into counterflow contact with the gas, with the result that not less than 99% by weight of the ethylene oxide contained in the reaction product gas is recovered. Through the top of the absorber 102, such gases as ethylene, oxygen, carbon dioxide, inert gases (nitrogen, argon, methane, and ethane), aldehydes, and oxidative substances which have escaped being absorbed are circulated via a conduit 104 to the step for absorption of carbon dioxide gas and/or the step of oxidation. At this step of absorption, such low-boiling impurities as formaldehyde and such high-boiling impurities as acetaldehyde and acetic acid which have been formed in the step for oxidation of ethylene besides ethylene, oxygen, carbon dioxide, and inert gases (nitrogen, argon, methane, and ethane), let alone ethylene oxide, are absorbed all at once in their substantial proportions.

The bottom liquid of the ethylene oxide absorber 102 is forwarded via a conduit 105 to a heat exchanger 106 and, through exchange of heat with the bottom liquid of the ethylene oxide stripper, allowed to reach an elevated temperature of 70° to 110° C., and then forwarded via a conduit 107 to a gas-liquid separation tank 108, with the result that the more voaltile component gas of the inert gases containing ethylene oxide and water is partly separated by a conduit 109. The remaining absorbent liquid which has been stripped of the more volatile component gas by flushing is introduced via a conduit 110 to the upper part of an ethylene oxide stripper 111 kept under a pressure of 0.1 to 2 kg/cm$^2$G at a temperature of 85° to 120° C. and heated therein by supplying a heating medium such as steam or a heat medium (product of The Dow Chemical Company and marketed under trademark designation of "Dowtherm") through a conduit 113 inside a reboiler 112 of the ethylene oxide stripper 111 or by introducing steam directly to the bottom of the ethylene oxide stripper 111, with the result that not less than 99% by weight of the ethylene oxide contained in the absorbent liquid is obtained through diffusion. From the bottom of the ethylene oxide stripper 111, part of the bottom liquid of the stripper containing substantially no ethylene oxide and having a temperature of 100° to 150° C. is introduced via conduits 114 and 115 to a heat exchanger 106 to exchange heat with the bottom liquid of the ethylene oxide absorber 102, passed through a conduit 116, further cooled in a cooler 117 having cooling water circulated via conduits 118 and 119 therein, then admixed with fresh water introduced via a conduit 121 for adjustment of the ethylene glycol concentration in the absorbent liquid, and admixed with an aqueous potassium hydroxide solution when necessary for adjustment of the pH of the absorbnt liquid. For adjustment of the anti-foam agent concentration in the absorbent liquid, the anti-foam agent may be introduced into the ethylene oxide absorber 102 by way of replenishment.

For the purpose of preventing the ethylene glycol by-produced in the hydrolysis of ethylene oxide and water, such low-boiling impurities as formaldehyde, and such high-boiling impurities as acetaldehyde and acetic acid from increasing in concentration in the absorbent liquid between the step for oxidation of ethylene with a molecular oxygen and the step for diffusion of ethylene oxide, the bottom liquid of the ethylene oxide stripper 111 is withdrawn from the bottom of the ethylene oxide stripper 111 via conduits 114 and 122 and forwarded to the step for concentration of by-produced ethylene glycol.

In the meantime, the ethylene oxide-containing vapor obtained through diffusion from the top of the ethylene oxide stripper 111 is forwarded via a conduit 123 to a reboiler 160 of the ethylene oxide refiner 150 to be used as a heat source therefore. The resulting condensate and the uncondensed vapor are forwarded via a conduit 161 to a condenser 164 having cooling water circuited via conduits 162 and 163 therein. The condensate is returned via a conduit 165 to the top of the ethylene oxide stripper 111 and the uncondensed vapor is introduced via a conduit 166 to the dehydrator 129.

The vapor received in the dehydrator 129 is heated by passing a heat medium such as steam or Dowtherm (product of The Dow Chemical Company) through a conduit 131 by the reboiler 130 or directly introducing steam into the lower part of the dehydrator 129. From the bottom of the dehydrator 129, the water containing substantially no ethylene oxide is withdrawn via a conduit 132.

From the top of the dehydrator 129, the vapor containing ethylene oxide is forwarded via a conduit 133 to a condenser 134 having cooling water or brine circulated via conduits 135 and 136 therein. Part of the condensate is returned via a conduit 137 to the top of the dehydrator 129 and the uncondensed vapor from the condenser 134 is introduced via a conduit 139 to an ethylene oxide vent-scrubber (not shown).

The other part of the condensate in the condenser 134 is introduced via a conduit 138 to a light ends stripper 140. From the top of the light ends stripper 140, the ethylene oxide vapor containing more volatile component gases is forwarded via a conduit 143 to a condenser 144. The condensate is returned via conduit 147 to the top of the light ends stripper 140. The uncondensed vapor is introduced via a conduit 148 to the ethylene oxide vent-scrubber (not shown) for recovery of ethylene oxide.

The bottom liquid of the light ends stripper 140 is introduced via a conduit 149 to the ethylene oxide refiner 150.

The diffusate from the top of the ethylene oxide stripper 111 is introduced to a reboiler 160 of the ethylene oxide refiner 150 and heated by a reboiler 158 of the ethylene oxide refiner 150 by having a heat medium such as steam or Dowtherm (product of The Dow Chemical Company) circulated via a conduit 159 therein. It is rectified with the bottom temperature of the ethylene oxide refiner controller in the range of 29° to 81° C. and the bottom pressure thereof in the range of 1.1 to 8.1 kg/cm$^2$G. From the top of the ethylene oxide refiner, the ethylene oxide vapor having a top temperature of 35° to 75° C. and a top pressure of 1 to 8 kg/cm$^2$G is forwarded via a conduit 151 to an ethylene oxide condenser 152 for liquefaction of ethylene oxide. Part of the liquefied ethylene oxide is returned via a conduit 156 to the top of the ethylene oxide refiner 150. The other part thereof is withdrawn as ethylene oxide product via a conduit 157.

The bottom of the ethylene oxide refiner 150 is withdrawn via a conduit 167 when necessary for separation of heavy-duty components of the high-boiling impurities such as acetaldehyde, water, acetic acid etc.

Figure 3:
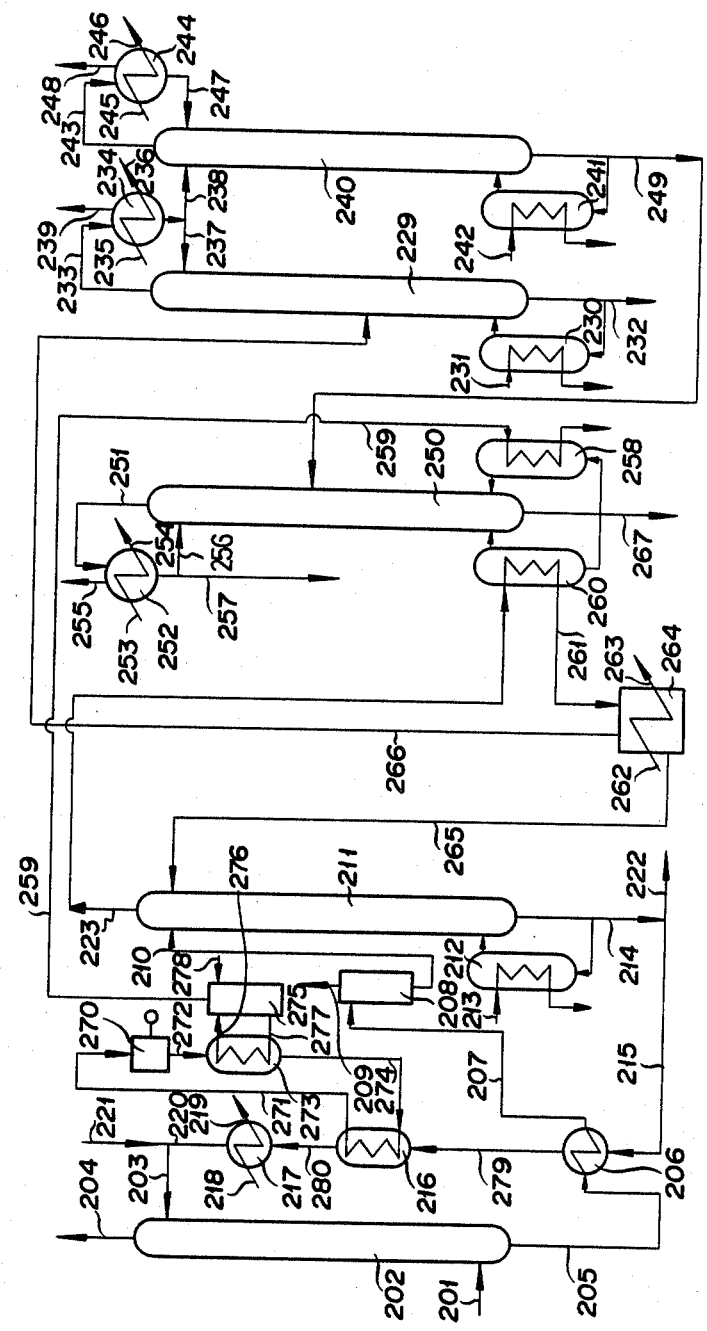
FIGS. 3 through 7 are flow charts illustrating other models of carrying out the method for the purification of ethylene oxide in accordance with the present invention.

FIG. 3 illustrates another embodiment of the present invention. In a method similar to that illustrated in FIG. 2, the bottom liquid of the ethylene oxide stripper which has exchanged heat with the liquid from the ethylene oxide absorber in a heat exchanger 206 is forwarded to a refrigerant vaporizer 216.

The refrigerant which has been vaporized in the refrigerant vaporizer 216 in consequence of the exchange of heat with the bottom liquid of the ethylene oxide stripper is forwarded via a conduit 271 to a compressor 270 to be compressed therein. The compressed refrigerant is forwarded via a conduit 272 to a refrigerant condenser 273 to be condensed therein through transfer of heat thereof to an external fluid. The condensed refrigerant is forwarded via a conduit 274 to the refrigerant vaporizer 216 again.

Steam can be recovered through a conduit 259 by circulating the water introduced via conduits 276 and 277 to the refrigerant condenser 273 and the water introduced via a conduit 278 to a tank 275. This recovered steam can be effectively utilized as a heat source for the step of ethylene oxide production. Particularly, this steam can be used as a heat source for the ethylene oxide refiner 250.

In FIG. 3, the reference numerals which are the sums of those of FIG. 2 each plus 100 denote similar members.

Figure 4:
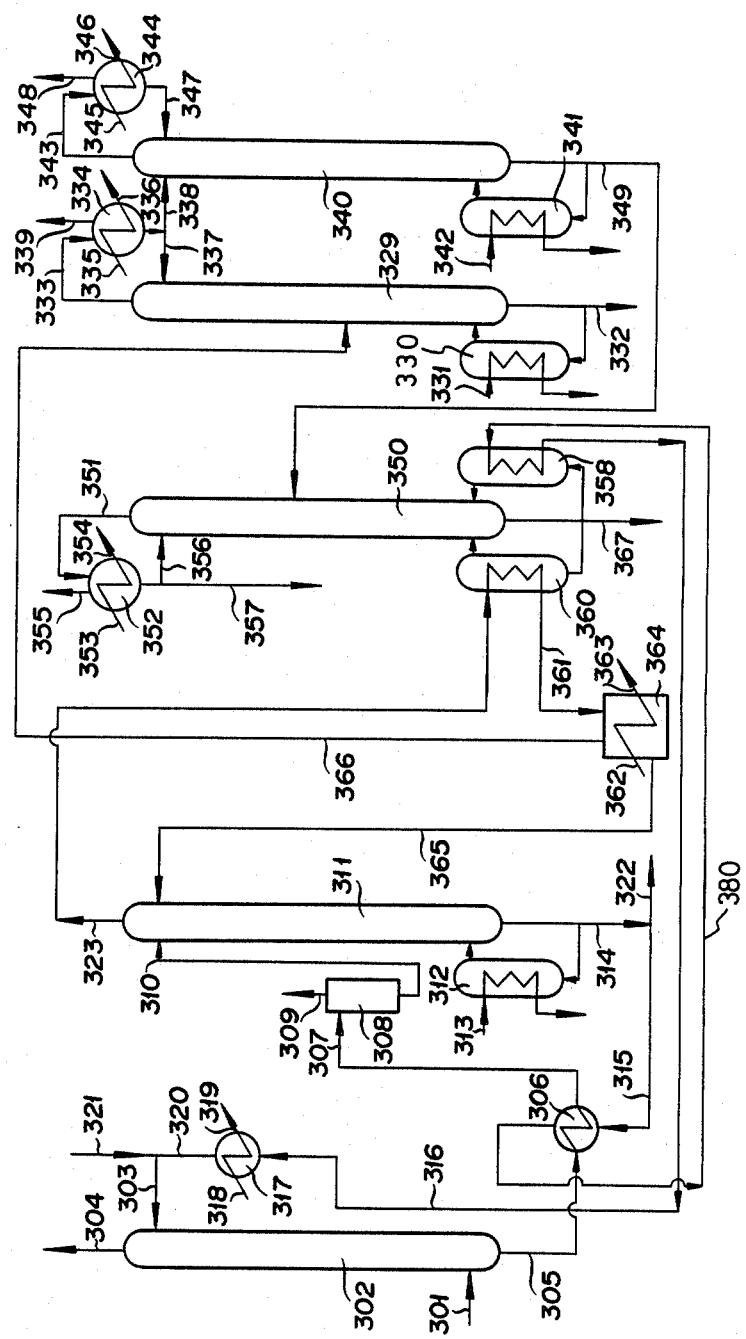

FIG. 4 illustrates yet another embodiment of the present invention. In a method similar to that illustrated in FIG. 2, the bottom liquid of the ethylene oxide stripper, after having exchanged heat with the liquid from the bottom of the ethylene oxide absorber 302 in a heat exchanger 306, is introduced via a conduit 380 to a reboiler 358 of an ethylene oxide refiner 350 to be used as a heat source therein, then forwarded via a conduit 316 to a cooler 317 to be cooled therein, and circulated via conduits 320 and 303 to an ethylene oxide absorber 302.

In FIG. 4, the reference numerals which are the sums of those of FIG. 2 each plus 200 denote similar members.

Figure 5:
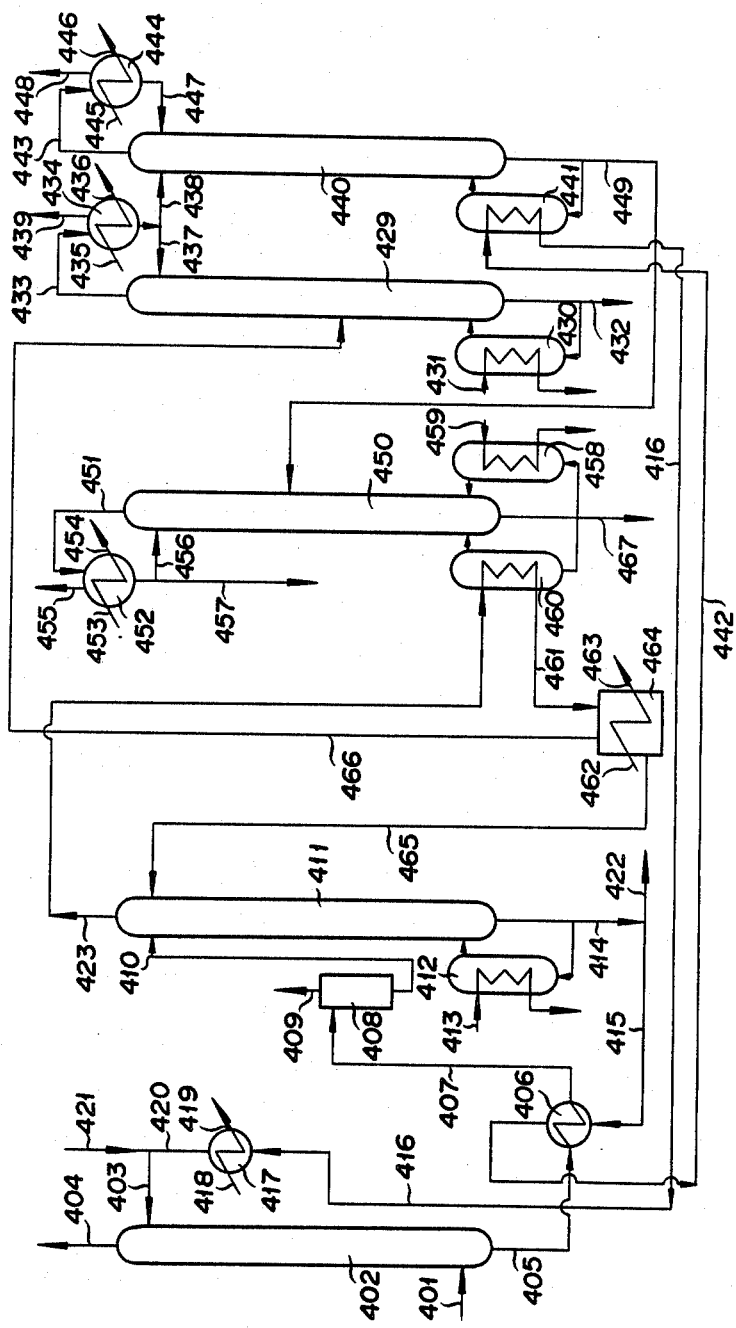

FIG. 5 illustrates a further embodiment of the present invention. In a method similar to that illustrated in FIG. 2, the bottom liquid of the ethylene oxide stripper is allowed to exchange heat with the liquid from the bottom of the ethylene oxide absorber 402 in a heat exchanger 406. The resulting liquid is introduced via conduit 442 to a reboiler 441 of a light ends stripper 440 to be used as a heat source therein, then forwarded via a conduit 416 to a cooler 417 to be cooled therein, and circulated via conduits 420 and 403 to the ethylene oxide absorber 402.

In FIG. 5, the reference numerals which are the sums of those of FIG. 2 each plus 300 denote similar members.

Figure 6:
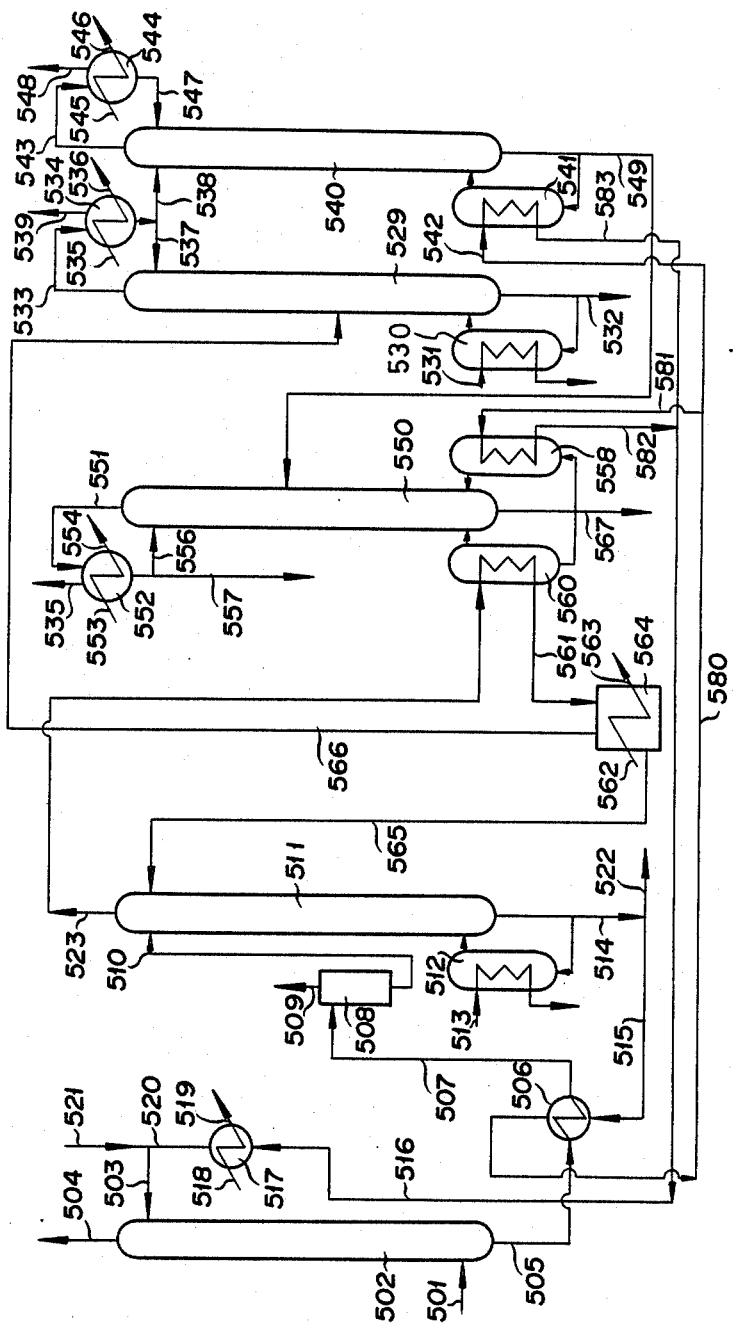

FIG. 6 illustrates yet another embodiment of the present invention. In a method similar to that of FIG. 2, the bottom liquid of the ethylene oxide stripper is caused to exchange heat with the liquid from the bottom of the ethylene oxide absorber 502 in a heat exchanger 506. The resulting liquid is introduced via conduits 580, 581, and 542 to a reboiler 558 of a refiner 550 and to a reboiler 541 of a light ends stripper 540 to be used as a heat source. It is then forwarded via conduits 582 and 583 to a cooler 517 to be cooled therein. The cooled liquid is circulated via conduits 520 and 503 to the ethylene oxide absorber 502.

In FIG. 6, the reference numerals which are the sums of those of FIG. 2 each plus 400 denote similar members.

Figure 7:
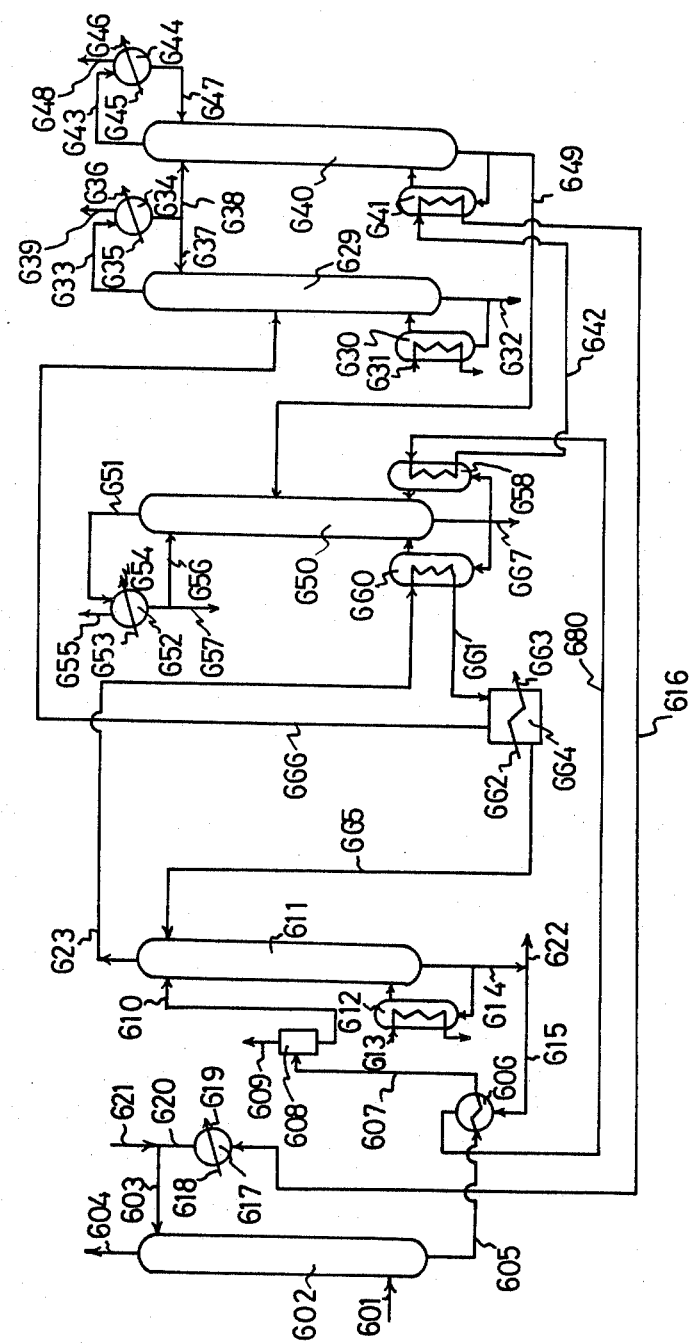

FIG. 7 illustrates another embodiment of the present invention. In a method similar to that of FIG. 2, the bottom liquid of the ethylene oxide stripper is caused to exchange heat with the liquid from the bottom of the ethylene oxide absorber 602 in a heat exchanger 606. The resulting liquid is introduced via a conduit 680 to a reboiler 658 of an ethylene oxide refiner 650 to be used as a heat source and then introduced via a conduit 642 to a reboiler 641 of a light ends stripper 640 to be used as a heat source. It is then forwarded via a conduit 616 to a cooler 617 to be cooled therein. The cooled liquid is circulated via conduits 620 and 603 to the ethylene oxide absorber 602.

In FIG. 7 the reference numerals which are the sums of those of FIG. 2 each plus 500 denote similar members.

Now, the present invention will be described more specifically below with reference to working examples. It should be noted, however, that this invention is not limited by these working examples.

EXAMPLE 1

As illustrated in FIG. 2, the gas produced by catalytic gas-phase oxidation of ethylene with a molecular oxygen-containing gas and consequently containing ethylene oxide was introduced via a conduit 101 to the lower part of the tray type ethylene oxide absorber 102. An absorbent liquid having a temperature of 29.6° C. and a pH 6 and composed of 9% by weight of ethylene glycol, 3 ppm of an anti-foam agent (water-soluble silicone emulsion), and the balance of water was introduced via a conduit 103 into the upper part of the ethylene oxide absorber 102 and brought into counterflow contact therein with the reaction product gas to effect recovery of not less than 99% by weight of the ethylene oxide contained in the reaction product gas. From the top of the ethylene oxide absorber 102, such gases as the ethylene which had escaped being absorbed, oxygen, carbon dioxide, inert gases (nitrogen, argon, methane, and ethane), aldehydes, and acidic substances were circulated via a conduit 104 to the step for absorption of carbon dioxide and/or the step for oxidation. In this step of absorption, the low-boiling impurities such as formaldehyde and the high-boiling impurities such as acetaldehyde and acetic acid which are formed in the step for oxidation of ethylene besides ethylene, oxygen, carbon dioxide, and inert gases (nitrogen, argon, methane, and ethane), let alone ethylene oxide, were absorbed at once in their substantial amount. The bottom liquid of the ethylene oxide absorber 102 was forwarded via a conduit 105 to a heat exchanger 106, there to exchange heat with the bottom liquid of an ethylene oxide stripper 111 and gain in temperature to 70° to 110° C. The hot liquid was forwarded via a conduit 107 to a gas-liquid separation tank 108. The more volatile component gases of the inert gases containing ethylene oxide and water were separated via a conduit 109. The absorbent liquid remaining after flushing the more volatile component gases was introduced via a conduit 110 to the upper part of an ethylene oxide stripper 111 having a top pressure of 0.1 to 2 kg/cm$^2$G and a tower top temperature of 85° to 120° C. In the ethylene oxide stripper 111, the absorbent liquid was heated by passing steam to the reboiler 112 so as to obtain not less than 99% by weight of the ethylene oxide contained in the absorbent liquid. From the bottom of the ethylene oxide stripper 111, part of the bottom liquid of the ethylene oxide stripper containing substantially no ethylene oxide and having a temperature of 113.8° C. was forwarded via conduits 114 and 115 to heat exchanger 106 to exchange heat with the bottom liquid of the ethylene oxide absorber 102. The resulting liquid was forwarded via a conduit 116 and cooled by a cooler 117 having cooling water circulated via conduits 118 and 119 therein. Then, fresh water was introduced via a conduit 121 for adjustment of the ethylene glycol concentration in the absorbent liquid. For the purpose of preventing the ethylene glycol by-produced in consequence of the hydrolysis of ethylene oxide and water, such low-boiling impurities as formaldehyde, and such high-boiling impurities as acetaldehyde, acetic acid etc. in the absorbent liquid between the step for oxidation of ethylene with molecular oxygen and the step for diffusion of ethylene oxide, the bottom liquid of the ethylene oxide stripper 111 was withdrawn via conduits 114 and 122 from the bottom of the ethylene oxide stripper 111 and was forwarded to the step for by-produced ethylene glycol concentration.

In the meantime, the ethylene oxide-containing vapor obtained from the top of the ethylene oxide stripper 111 was forwarded via a conduit 123 to a reboiler 160 of an ethylene oxide refiner 150 to be used as a heat source therein. The resulting condensate was forwarded via a conduit 161 to a condenser 164 having cooling water circulated via conduits 162 and 163 therein. The condensate was returned via a conduit 165 to the top of the ethylene oxide stripper 111. The uncondensed vapor was introduced via a conduit 166 to a dehydrator 129.

By a reboiler 130 of the dehydrator 129, the fed vapor was heated by passing a steam through a conduit 131. From the bottom of the dehydrator 129, the water containing substantially no ethylene oxide was withdrawn via a conduit 132.

From the top of the dehydrator 129, the vapor containing ethylene oxide was forwarded via a conduit 133 to a condenser 134 having chilled water circulated via conduits 135 and 136 therein. Part of the resulting condensate was returned via a conduit 137 to the top of the dehydrator 129. The uncondensed vapor in the condenser 134 was introduced via a conduit 139 to an ethylene oxide vent-scrubber (not shown). The other part of the condensate was introduced via a conduit 138 to a light ends stripper 140. From the top of the more light ends stripper 140, the ethylene oxide vapor containing more volatile component gases was forwarded via a conduit 143 to a condenser 144. The resulting condensate was returned via a conduit 147 to the light ends stripper 140. The uncondensed vapor was introduced via a conduit 148 to the ethylene oxide vent-scrubber (not shown) for recovery of ethylene oxide. The bottom liquid of the light ends stripper 140 was introduced via a conduit 149 to an ethylene oxide refiner 150.

The diffusate from the ethylene oxide stripper 111 was introduced to a reboiler 160 of the ethylene oxide refiner 150 and heated by a reboiler 158 of the ethylene oxide refiner 150 by passing a steam via a conduit 159 therein. The diffusate was recitified with the bottom temperature of the ethylene oxide refiner controlled at 45° C. and the bottom pressure thereof at 2.0 kg/cm$^2$G. From the top of the ethylene oxide refiner, the ethylene oxide vapor having a top temperature of 39° C. and a top pressure of 1.8 kg/cm$^2$G was forwarded via a conduit 151 to an ethylene oxide condenser 152 to liquefy ethylene oxide. Part of the liquefied ethylene oxide was returned via a conduit 156 to the top of the ethylene oxide refiner 150. The other part of the liquefied ethylene oxide was withdrawn as ethylene oxide product via a conduit 157.

The uncondensed vapor in the ethylene oxide condenser 152 was introduced via a conduit 155 to the ethylene oxide vent-scrubber (not shown) for recovery of ethylene oxide.

The bottom liquid of the ethylene oxide refiner 150 was withdrawn via a conduit 167 for the separation of heavy-duty components of such high boiling impurities as acetaldehyde, water, acetic acid etc.

Table 1 shows collectively the conditions for continuous operation of this process.

EXAMPLE 2

As illustrated in FIG. 3, in a method similar to that of Example 1, the bottom liquid of the ethylene oxide stripper 211 was introduced via conduits 214 and 215 to a heat exchanger 206, and caused to exchange heat with the liquid from the bottom of the ethylene oxide absorber 201. The resulting liquid was forwarded to a refrigerant evaporator 216 and then to a cooler 217 to be cooled therein. The cooled liquid was circulated via conduits 220 and 203 to the ethylene oxide absorber 202.

The refrigerant vaporized in a refrigerant vaporizer 216 in consequence of exchange of heat with the bottom liquid of the ethylene oxide stripper 211 was forwarded via a conduit 271 to a refrigerant compressor 270 to be compressed therein. The compressed refrigerant was forwarded via a conduit 272 to a refrigerant condenser 273 to be condensed therein through release of heat to an external fluid. The condensed refrigerant was forwarded via a conduit 274 again to the refrigerant vaporizer 216.

By a conduit 259, steam was recovered by circulating the water introduced via conduits 276 and 277 into the refrigerant condenser 273 and the water introduced via a conduit 278 into a tank 275. The recovered steam was forwarded to a reboiler 258 of an ethylene oxide refiner 250 to be used as a heat source therein.

Table 2 shows collectively the conditions for continuous operation of this process.

EXAMPLE 3

As illustrated in FIG. 4, in a method similar to that of Example 1, the bottom liquid of an ethylene oxide stripper was caused to exchange heat with the liquid from an ethylene oxide absorber 302 in a heat exchanger 306. The resulting liquid was introduced via a conduit 380 to a reboiler 358 of an ethylene oxide refiner 350 and used as a heat source therefor. Then, it was forwarded via a conduit 316 to a cooler 317 to be cooled therein and further circulated via conduits 320 and 303 to the ethylene oxide absorber 302. In all the other respects, the method of Example 1 was faithfully repeated.

Table 3 shows collectively the conditions for continuous operation of this process.

EXAMPLE 4

As illustrated in FIG. 5, in a method similar to that of Example 1, the bottom liquid of an ethylene oxide stripper was caused to exchange heat with the liquid from an ethylene oxide absorber 402 in a heat exchanger 406. The resulting liquid was introduced via a conduit 442 to a heat exchanger 441 of a light ends stripper 440 and used as a heat source therein. It was then sent through a conduit 416 to a cooler 417 to be cooled therein and further circulated via conduits 420 and 403 to the ethylene oxide absorber 402. In all the other respects, the method of Example 1 was faithfully repeated.

Table 4 shows collectively the conditions for continuous operation of this process.

EXAMPLE 5

As illustrated in FIG. 6, in a method similar to that of Example 1, the bottom liquid of an ethylene oxide stripper was caused to exchange heat with the liquid from an ethylene oxide absorber 502. The resulting liquid was introduced via conduits 580 and 581 to a reboiler 558 of an ethylene oxide refiner 550 and introduced via conduits 580 and 542 to a reboiler 541 of a light ends stripper 540 respectively to be used as a heat source therefor. It was then forwarded via conduits 582 and 516 or via conduits 583 and 516 to a cooler 517 to be cooled therein and circulated via conduits 520 and 503 to the ethylene oxide absorber 502. In all the other respects, the method of Example 1 was faithfully repeated.

Table 5 shows collectively the conditions for continuous operation of this process.

EXAMPLE 6

The procedure of Example 5 was repeated, except that the conditions for the operation of component parts were varied. The results were as shown in Table 6.

EXAMPLE 7

As illustrated in FIG. 7, in a method similar to that of Example 1, the bottom liquid of an ethylene oxide stripper was caused to exchange heat with the liquid from the bottom of an ethylene oxide absorber 602 in a heat exchanger 606. The resulting liquid was introduced via a conduit 680 to a reboiler 658 of an ethylene oxide refiner 650 and used as a heat source therefore. Then, it was sent via a conduit 642 to a reboiler 641 of a light ends stripper 640 and used as a heat source again. It was forwarded via a conduit 616 to a cooler 617 to be cooled therein and circulated via conduits 620 and 603 to the ethylene oxide absorber 602. In all the other respects, the method of Example 1 was faithfully repeated.

Table 7 shows collectively the conditions for continuous operation of this process. Control As illustrated in FIG. 1, in a method similar to that of Example 1, the ethylene oxide-containing vapor obtained through diffusion from the top of an ethylene oxide stripper 11 was forwarded via a conduit 23 to a condenser 24 having cooling water circulated via conduits 25 and 26 therein. The resulting condensate was returned via a conduit 27 to the top of the ethylene oxide stripper 11. The uncondensed vapor was introduced via a conduit 28 to a dehydrator 29.

By a reboile 30 of the dehydrator 29, the vapor was heated by passing a heat medium such as steam through a conduit 31 therein. From the bottom of the dehydrator 29, the water containing no ethylene oxide was withdrawn via a conduit 32. In all the other respects, the method of Example 1 was followed.

Table 8 shows collectively the conditions for continuous operation of this process.

TABLE 1

| | | | | | | | | | Composition (% by weight) | |
|---|---|---|---|---|---|---|---|---|---|---|
| Component part | 107 | 109 | 110 | 113 | 115 | 116 | 118 | 119 | 123 | 149 |
| Inert gas | 0.06 | 24.22 | | | | | | | | |
| Carbon dioxide gas | 0.11 | 30.10 | 0.04 | | | | | | 0.67 | |
| Ethylene oxide | 2.73 | 30.34 | 2.60 | | | | | | 52.95 | 99.97 |
| Water | 88.46 | 15.34 | 88.62 | | 91.00 | 91.00 | | | 46.34 | 0.01 |
| Ethylene glycol | 8.64 | | 8.74 | | 9.00 | 9.00 | | | 0.04 | |
| Others | | | | | | | | | | 0.02 |
| Flow rate (kg/Hr) | 308100 | 810 | 307290 | | 295600 | 295600 | | | 15500 | 7600 |
| Pressure (kg/cm$^2$G) | 3.4 | 3.4 | 3.4 | 2.2 | 0.5 | 5 | 3 | 3 | 0.4 | 5 |
| Temperature (°C.) | 105.5 | 104.7 | 104.7 | 135 | 113.8 | 56.5 | 25 | 40 | 99.6 | 64 |
| Steam (kg/Hr) | | | | 14900 | | | | | | |
| Cooling water (m$^3$/Hr) | | | | | | | 510 | 510 | | |
| Component part | | | 162 | 163 | 165 | 166 | 156 | 157 | 159 | |
| Inert gas | | | | | | | | | | |
| Carbon dioxide gas | | | | | | 1.27 | | | | |
| Ethylene oxide | | | | | 4.88 | 95.75 | ≃100 | ≃100 | | |
| Water | | | | | 95.12 | 2.98 | | | | |

TABLE 1-continued

|  | Composition (% by weight) | | | | | | |
|---|---|---|---|---|---|---|---|
| Ethylene glycol | | | | | | | |
| Others | | | | | | | |
| Flow rate (kg/Hr) | | | 7300 | 8200 | 23400 | 7594 | |
| Pressure (kg/cm$^2$G) | 3 | 3 | 0.3 | 0.3 | 3.5 | 3.5 | 2.2 |
| Temperature (°C.) | 25 | 35 | 45 | 45 | 35 | 35 | 135 |
| Steam (kg/Hr) | | | | | | | 1260 |
| Cooling water (m$^3$/Hr) | 63 | 63 | | | | | |

TABLE 2

| | Composition (% by weight) | | | | | | | | | |
|---|---|---|---|---|---|---|---|---|---|---|
| Component part | 207 | 209 | 210 | 213 | 215 | 279 | 280 | 259 | 220 | 218 |
| Inert gas | 0.06 | 24.22 | | | | | | | | |
| Carbon dioxide gas | 0.11 | 30.10 | 0.04 | | | | | | | |
| Ethylene oxide | 2.73 | 30.34 | 2.60 | | | | | | | |
| Water | 88.46 | 15.34 | 88.62 | | 91.00 | 91.00 | 91.00 | | 91.00 | |
| Ethylene glycol | 8.64 | | 8.74 | | 9.00 | 9.00 | 9.00 | | 9.00 | |
| Others | | | | | | | | | | |
| Flow rate (kg/Hr) | 308100 | 810 | 307290 | | 295600 | 295600 | 295600 | | 295600 | |
| Pressure (kg/cm$^2$G) | 3.4 | 3.4 | 3.4 | 2.2 | 0.5 | 5 | 5 | −0.64 | 5 | 3 |
| Temperature (°C.) | 105.5 | 104.7 | 104.7 | 135 | 113.8 | 56.5 | 54.4 | 75 | 29.8 | 25 |
| Steam (kg/Hr) | | | | 14900 | | | | 1170 | | |
| Cooling water (m$^3$/Hr) | | | | | | | | | | 475 |

| | | | | | | | | |
|---|---|---|---|---|---|---|---|---|
| Component part | 219 | 223 | 249 | 262 | 263 | 265 | 266 | 256 | 257 |
| Inert gas | | | | | | | | | |
| Carbon dioxide gas | | 0.67 | | | | | 1.27 | | |
| Ethylene oxide | | 52.95 | 99.97 | | | 4.88 | 95.75 | ≃100 | ≃100 |
| Water | | 46.34 | 0.01 | | | 95.12 | 2.98 | | |
| Ethylene glycol | | 0.04 | | | | | | | |
| Others | | | 0.02 | | | | | | |
| Flow rate (kg/Hr) | | 15500 | 7600 | | | 7300 | 8200 | 23400 | 7594 |
| Pressure (kg/cm$^2$G) | 3 | 0.4 | 5 | 3 | 3 | 0.3 | 0.3 | 3.5 | 3.5 |
| Temperature (°C.) | 40 | 99.6 | 64 | 25 | 35 | 45 | 45 | 35 | 35 |
| Steam (kg/Hr) | | | | | | | | | |
| Cooling water (m$^3$/Hr) | 475 | | | 63 | 63 | | | | |

TABLE 3

| | Composition (% by weight) | | | | | | | | | |
|---|---|---|---|---|---|---|---|---|---|---|
| Component part | 307 | 309 | 310 | 313 | 315 | 380 | 316 | 318 | 319 | 320 |
| Inert gas | 0.06 | 24.22 | | | | | | | | |
| Carbon dioxide gas | 0.11 | 30.10 | 0.04 | | | | | | | |
| Ethylene oxide | 2.73 | 30.34 | 2.60 | | | | | | | |
| Water | 88.46 | 15.34 | 88.62 | | 91.00 | 91.00 | 91.00 | | | 91.00 |
| Ethylene glycol | 8.64 | | 8.74 | | 9.00 | 9.00 | 9.00 | | | 9.00 |
| Others | | | | | | | | | | |
| Flow rate (kg/Hr) | 308100 | 810 | 307290 | | 295600 | 295600 | 295600 | | | 295600 |
| Pressure (kg/cm$^2$G) | 3.4 | 3.4 | 3.4 | 2.2 | 0.5 | 5 | 5 | 3 | 3 | 5 |
| Temperature (°C.) | 105.5 | 104.7 | 104.7 | 135 | 113.8 | 56.5 | 54.4 | 25 | 40 | 29.6 |
| Steam (kg/Hr) | | | | 14900 | | | | | | |
| Cooling water (m$^3$/Hr) | | | | | | | | 475 | 475 | |

| | | | | | | | | |
|---|---|---|---|---|---|---|---|---|
| Component part | 323 | 362 | 363 | 365 | 366 | 349 | 356 | 357 |
| Inert gas | | | | | | | | |
| Carbon dioxide gas | 0.67 | | | | 1.27 | | | |
| Ethylene oxide | 52.95 | | | 4.88 | 95.75 | 99.97 | ≃100 | ≃100 |
| Water | 46.34 | | | 95.12 | 2.98 | 0.01 | | |
| Ethylene glycol | 0.04 | | | | | | | |
| Others | | | | | | 0.02 | | |
| Flow rate (kg/Hr) | 15500 | | | 7300 | 8200 | 7600 | 23400 | 7594 |
| Pressure | 0.4 | 3 | 3 | 0.3 | 0.3 | 5 | 1.8 | 1.8 |

TABLE 3-continued

|  |  |  |  |  |  | Composition (% by weight) | | |
|---|---|---|---|---|---|---|---|---|
| (kg/cm²G) |  |  |  |  |  |  |  |  |
| Temperature (°C.) | 99.6 | 25 | 35 | 45 | 45 | 64 | 39 | 39 |
| Steam (kg/Hr) |  |  |  |  |  |  |  |  |
| Cooling water (m³/Hr) |  | 63 | 63 |  |  |  |  |  |

TABLE 4

|  |  |  |  |  |  |  | Composition (% by weight) | | |
|---|---|---|---|---|---|---|---|---|---|
| Component part | 407 | 409 | 410 | 413 | 415 | 442 | 416 | 418 | 419 | 420 |
| Inert gas | 0.06 | 24.22 |  |  |  |  |  |  |  |  |
| Carbon dioxide gas | 0.11 | 30.10 | 0.04 |  |  |  |  |  |  |  |
| Ethylene oxide | 2.73 | 30.34 | 2.60 |  |  |  |  |  |  |  |
| Water | 88.46 | 15.34 | 88.62 |  | 91.00 | 91.00 | 91.00 |  |  | 91.00 |
| Ethylene glycol | 8.64 |  | 8.74 |  | 9.00 | 9.00 | 9.00 |  |  | 9.00 |
| Others |  |  |  |  |  |  |  |  |  |  |
| Flow rate (kg/Hr) | 308100 | 810 | 307290 |  | 295600 | 295600 | 295600 |  |  | 295600 |
| Pressure (kg/cm²G) | 3.4 | 3.4 | 3.4 | 2.2 | 0.5 | 5 | 5 | 3 | 3 | 5 |
| Temperature (°C.) | 105.5 | 104.7 | 104.7 | 135 | 113.8 | 56.5 | 53.8 | 25 | 40 | 29.6 |
| Steam (kg/Hr) |  |  |  | 14900 |  |  |  |  |  |  |
| Cooling water (m³/Hr) |  |  |  |  |  |  |  | 460 | 460 |  |

| Component part | 423 | 462 | 463 | 465 | 466 | 449 | 456 | 451 | 459 |
|---|---|---|---|---|---|---|---|---|---|
| Inert gas |  |  |  |  |  |  |  |  |  |
| Carbon dioxide gas | 0.67 |  |  |  | 1.27 |  |  |  |  |
| Ethylene oxide | 52.95 |  |  | 4.88 | 95.75 | 99.97 | ≃100 | ≃100 |  |
| Water | 46.34 |  |  | 95.12 | 2.98 | 0.01 |  |  |  |
| Ethylene glycol | 0.04 |  |  |  |  |  |  |  |  |
| Others |  |  |  |  |  | 0.02 |  |  |  |
| Flow rate (kg/Hr) | 15500 |  |  | 7300 | 8200 | 7600 | 23400 | 7594 |  |
| Pressure (kg/cm²G) | 0.4 | 3 | 3 | 0.3 | 0.3 | 2.4 | 3.5 | 3.5 | 2.2 |
| Temperature (°C.) | 99.6 | 25 | 35 | 45 | 45 | 45 | 35 | 35 | 135 |
| Steam (kg/Hr) |  |  |  |  |  |  |  |  | 1400 |
| Cooling water (m³/Hr) |  | 63 | 63 |  |  |  |  |  |  |

TABLE 5

|  |  |  |  |  |  |  | Unit (kg mol/Hr) | |
|---|---|---|---|---|---|---|---|---|
| Component part | 505 | 509 | 513 | 514 | 516 | 523 | 532 | 538 |
| Inert gas | 4.97 | 4.80 |  |  |  | 0.17 |  |  |
| Carbon dioxide gas | 9.41 | 6.97 |  |  |  | 2.44 |  | 1.44 |
| Ethylene oxide | 283.74 | 12.42 |  | 0.16 | 0.15 | 277.27 |  | 258.08 |
| Water | 19164.0 | 13.27 |  | 20066.0 | 18480.01 | 426.00 | 45.34 | 0.01 |
| Ethylene glycol | 116.52 |  |  | 126.52 | 116.52 | 0.03 |  |  |
| Others |  |  |  |  |  |  |  |  |
| Flow rate (kg-mol/Hr) | 19578.64 | 37.46 |  | 20192.68 | 18596.68 | 705.91 | 45.34 | 259.53 |
| Pressure (kg/cm²abs) | 6 | 3 | 3.2 | 1.5 | 5 | 1.4 | 1.4 | 4 |
| Temperature (°C.) | 52.5 | 101 | 135 | 111 | 49.2 | 94.6 | 108.8 | 8 |
| Steam (kg/Hr) |  |  | 17485 |  |  |  |  |  |
| Cooling water (m³/Hr) |  |  |  |  |  |  |  |  |

| Component part | 539 | 565 | 566 | 548 | 549 | 557 | 567 | 580 |
|---|---|---|---|---|---|---|---|---|
| Inert gas | 0.17 |  | 0.17 |  |  |  |  |  |
| Carbon dioxide gas | 1.00 |  | 2.44 | 1.44 |  |  |  |  |
| Ethylene oxide | 3.07 | 16.12 | 261.15 | 3.80 | 254.28 | 249.29 | 4.99 | 0.15 |
| Water |  | 380.65 | 45.35 |  | 0.01 |  | 0.01 | 18480.01 |
| Ethylene glycol |  | 0.03 |  |  |  |  |  | 116.52 |
| Others |  |  |  |  |  |  |  |  |
| Flow rate (kg-mol/Hr) | 4.24 | 396.80 | 309.11 | 5.24 | 254.29 | 249.29 | 5.00 | 18596.68 |
| Pressure (kg/cm²abs) | 1.3 | 6 | 1.35 | 1.3 | 1.4 | 2.5 | 2.9 | 5 |
| Temperature (°C.) | 8 | 60.1 | 60 | 8 | 18 | 35 | 39.7 | 60.2 |
| Steam (kg/Hr) |  |  |  |  |  |  |  |  |
| Cooling water |  |  |  |  |  |  |  |  |

TABLE 5-continued

|  | Unit (kg mol/Hr) |
| --- | --- |
| (m³/Hr) | |

TABLE 6

Unit (kg mol/Hr)

| Component part | 505 | 509 | 513 | 514 | 516 | 523 | 532 | 538 |
| --- | --- | --- | --- | --- | --- | --- | --- | --- |
| Inert gas | 4.97 | 4.85 | | | | 0.12 | | |
| Carbon dioxide gas | 9.41 | 7.50 | | | | 1.91 | | 1.20 |
| Ethylene oxide | 283.74 | 17.24 | | 0.17 | 0.15 | 276.11 | | 242.01 |
| Water | 19164.0 | 26.98 | | 20632.0 | 17609.44 | 245.74 | 16.94 | 0.02 |
| Ethylene glycol | 116.52 | | | 136.52 | 116.52 | 0.03 | | |
| Others | | | | | | | | |
| Flow rate (kg-mol/Hr) | 19578.64 | 56.57 | | 20768.69 | 17726.11 | 523.91 | 16.94 | 243.23 |
| Pressure (kg/cm²bs) | 6 | 3.0 | 3.2 | 3.1 | 5 | 3.0 | 3.0 | 4 |
| Temperature (°C.) | 52.5 | 105.6 | 135 | 134.5 | 77.4 | 108.4 | 133 | 34 |
| Steam (kg/Hr) | | | 28387 | | | | | |
| Cooling water (m³/Hr) | | | | | | | | |

| Component part | 539 | 548 | 549 | 557 | 565 | 566 | 567 | 580 |
| --- | --- | --- | --- | --- | --- | --- | --- | --- |
| Inert gas | 0.12 | | | | | 0.12 | | |
| Carbon dioxide gas | 0.71 | 1.20 | | | | 1.91 | | |
| Ethylene oxide | 4.32 | 3.02 | 238.99 | 234.01 | 29.78 | 246.33 | 4.98 | 0.15 |
| Water | | | 0.02 | | 228.78 | 16.96 | 0.02 | 17609.44 |
| Ethylene glycol | | | | | 0.03 | | | 116.52 |
| Others | | | | | | | | |
| Flow rate (kg-mol/Hr) | 5.15 | 4.22 | 239.01 | 234.01 | 258.59 | 265.32 | 5.00 | 17726.11 |
| Pressure (kg/cm²bs) | 2.9 | 3.5 | 3.6 | 2.5 | 6.0 | 2.95 | 2.9 | 5 |
| Temperature (°C.) | 34 | 35 | 46.7 | 35 | 60 | 60 | 39.7 | 63.6 |
| Steam (kg/Hr) | | | | | | | | |
| Cooling water (m³/Hr) | | | | | | | | |

TABLE 7

Composition (% by weight)

| Component part | 607 | 609 | 610 | 613 | 615 | 680 | 642 | 616 | 618 | 619 |
| --- | --- | --- | --- | --- | --- | --- | --- | --- | --- | --- |
| Inert gas | 0.06 | 24.22 | | | | | | | | |
| Carbon dioxide gas | 0.11 | 30.10 | 0.04 | | | | | | | |
| Ethylene oxide | 2.73 | 30.34 | 2.60 | | | | | | | |
| Water | 88.46 | 15.34 | 88.62 | | 91.00 | 91.00 | 91.00 | 91.00 | | |
| Ethylene glycol | 8.64 | | 8.74 | | 9.00 | 9.00 | 9.00 | 9.00 | | |
| Others | | | | | | | | | | |
| Flow rate (kg/Hr) | 308100 | 810 | 307290 | | 295600 | 295600 | 295600 | 295600 | | |
| Pressure (kg/cm²G) | 3.4 | 3.4 | 3.4 | 2.2 | 0.5 | 5 | 5 | 5 | 3 | 3 |
| Temperature (°C.) | 105.5 | 104.7 | 104.7 | 135 | 113.8 | 56.5 | 54.2 | 51.5 | 25 | 40 |
| Steam (kg/Hr) | | | | 14900 | | | | | | |
| Cooling water (m³/Hr) | | | | | | | | | 415 | 415 |

| Component part | 620 | 623 | 662 | 663 | 665 | 666 | 649 | 656 | 657 |
| --- | --- | --- | --- | --- | --- | --- | --- | --- | --- |
| Inert gas | | | | | | | | | |
| Carbon dioxide gas | | 0.67 | | | | 1.27 | | | |
| Ethylene oxide | | 52.95 | | | 4.88 | 95.75 | 99.97 | ≈100 | ≈100 |
| Water | 91.00 | 46.34 | | | 95.12 | 2.98 | 0.01 | | |
| Ethylene glycol | 9.00 | 0.04 | | | | | | | |
| Others | | | | | | | 0.02 | | |
| Flow rate (kg/Hr) | 295600 | 15500 | | | 7300 | 8200 | 7600 | 23400 | 7594 |
| Pressure (kg/cm²G) | 5 | 0.4 | 3 | 3 | 0.3 | 0.3 | 2.4 | 1.8 | 1.8 |
| Temperature (°C.) | 29.5 | 99.6 | 25 | 35 | 45 | 45 | 45 | 39 | 39 |
| Steam (kg/Hr) | | | | | | | | | |
| Cooling water (m³/Hr) | | | 63 | 63 | | | | | |

TABLE 8

| | | | | | | | | | | | | | | | | Composition (% by weight) |
|---|---|---|---|---|---|---|---|---|---|---|---|---|---|---|---|---|
| Component part | 7 | 9 | 10 | 13 | 16 | 18 | 19 | 42 | 23 | 25 | 26 | 28 | 49 | 56 | 57 | 59 |
| Inert gas | 0.06 | 24.22 | | | | | | | | | | | | | | |
| Carbon dioxide gas | 0.11 | 30.10 | 0.04 | | | | | | 0.67 | | | 1.27 | | | | |
| Ethylene oxide | 2.73 | 30.34 | 2.60 | | | | | | 52.95 | | | 95.75 | 99.97 | ≃100 | ≃100 | |
| Water | 88.46 | 15.34 | 88.62 | | 91.00 | | | | 46.34 | | | 2.98 | 0.01 | | | |
| Ethylene glycol | 8.64 | | 8.74 | | 9.00 | | | | 0.04 | | | | | | | |
| Others | | | | | | | | | | | | | 0.02 | | | |
| Flow rate (kg/Hr) | 308100 | 810 | 307290 | | 295600 | | | | 15500 | | | 8200 | 7600 | 23400 | 7594 | |
| Pressure (kg/cm²G) | 3.4 | 3.4 | 3.4 | 2.2 | 5 | 3 | 3 | 2.2 | 0.4 | 3 | 3 | 0.3 | 5 | 3.5 | 3.5 | 2.2 |
| Temperature (°C.) | 105.5 | 104.7 | 104.7 | 135 | 56.5 | 25 | 40 | 135 | 99.6 | 25 | 35 | 45 | 64 | 35 | 35 | 135 |
| Steam (kg/Hr) | | | | 14900 | | | | 1500 | | | | | | | | 8000 |
| Cooling water (m³/Hr) | | | | | | 510 | 510 | | | 410 | 410 | | | | | |

The method of this invention manifests an effect of permitting generous reduction in the volume of external heat required in heating the ethylene oxide refiner by introducing the thermal energy of the vapor obtained through diffusion from the top of the ethylene oxide stripper into the reboiler of the ethylene oxide refiner. Further by working the method of this invention, there is manifested effects of lowering the thermal load on the cooling water used in cooling the vapor phase generated in the top of the ethylene oxide stripper and on the cooling water used in cooling the bottom liquid of the ethylene oxide stripper.

What is claimed is:

1. In a method for the purification of ethylene oxide by the steps of introducing the gas formed by catalytic gas-phase oxidation of ethylene with a molecular oxygen-containing gas said resultant gas containing ethylene oxide into an ethylene oxide absorber and leading said gas into counterflow contact therein with an absorbent liquid,
   recycling the residual gas emanating from the top of said ethylene oxide absorber to the reactor for said oxidation of ethylene,
   preheating an ethylene oxide-containing bottom liquid by heat-exchanging with a bottom liquid of an ethylene oxide stripper,
   supplying the preheated ethylene oxide via the top of said stripper,
   condensing the resulting vapors containing ethylene oxide and water,
   separating the water from a distillate in a dehydrator,
   separating a more volatile component from said distillate in a light ends stripper, and
   subsequently rectifying the thus obtained ethylene oxide fraction in an ethylene oxide refiner the improvement comprising:
   introducing a more volatile component obtained from said ethylene oxide stripper having 0.3–0.6 kg/cm²G pressure and temperature of 85° to 120° C. at its top, as a heat source for said ethylene oxide refiner; introducing said more volatile component into a condenser to provide
   a condensed liquid which is circulated to said ethylene oxide stripper, and
   an uncondensed vapor which is introduced into a dehydration tower; introducing a bottom liquid of said ethylene oxide stripper as a heat source for at least one apparatus component selected from the group consisting of ethylene oxide refiner and light ends stripper, wherein the ethylene oxide concentration in the bottom of said ethylene oxide stripper is not more than 0.5 ppm; and
   recycling said bottom liquid into said absorber as the absorbent liquid.

2. A method according to claim 1 wherein the bottom temperature of said ethylene oxide stripper is in the range of 100° to 150° C.

3. A method according to claim 1, wherein the absorbent liquid is passed to a heat pump to generate steam and use the steam as a heat source for the catalytic gas phase oxidation of ethylene with a molecular oxygen-containing gas for the production of ethylene oxide.

4. A method of claim 1 wherein bottom liquid of said ethylene oxide stripper is used as a heat source for said ethylene oxide refiner.

5. A method according to claim 4, wherein the absorbent liquid is passed to a heat pump to generate steam and use the steam as a heat source for the catalytic gas phase oxidation of ethylene with a molecular oxygen-containing as for the production of ethylene oxide.

6. A method of claim 1 wherein bottom liquid of said ethylene oxide stripper is used as a heat source for said light ends stripper.

7. A method according to claim 6, wherein the absorbent liquid is passed to a heat pump to generate steam and use the steam as a heat source for the catalytic gas phase oxidation of ethylene with a molecular oxygen-containing gas for the production of ethylene oxide.

8. A method of claim 1 wherein bottom liquid of said ethylene oxide stripper is used as a heat source for said ethylene oxide refiner and said light ends stripper.

9. A method according to claim 8, wherein the absorbent liquid is passed to a heat pump to generate steam and use the steam as a heat source for the catalytic gas phase oxidation of ethylene with a molecular oxygen-containing gas for the production of ethylene oxide.

10. A method of claim 1 wherein bottom liquid of said ethylene oxide stripper is used as a heat source for said ethylene oxide refiner and then said light ends stripper.

11. A method according to claim 10, wherein the absorbent liquid is passed to a heat pump to generate steam and use the steam as a heat source for the catalytic gas phase oxidation of ethylene with a molecular oxygen-containing gas for the production of ethylene oxide.

* * * * *

UNITED STATES PATENT AND TRADEMARK OFFICE
CERTIFICATE OF CORRECTION

PATENT NO.  : 4,778,567

DATED       : October 18, 1988

INVENTOR(S) : Yukihiko Kakimoto, et al

It is certified that error appears in the above-identified patent and that said Letters Patent is hereby corrected as shown below:

On the title page, Assignee;

Atochem 4, Paris, France

Signed and Sealed this

Twenty-sixth Day of February, 1991

Attest:

HARRY F. MANBECK, JR.

*Attesting Officer*      *Commissioner of Patents and Trademarks*